US00PP19276P3

(12) United States Plant Patent

Tupy et al.

(10) Patent No.: US PP19,276 P3

(45) Date of Patent: Sep. 30, 2008

(54) APPLE TREE NAMED 'ORION'

(50) Latin Name: *Malus Mill*
Varietal Denomination: Orion

(75) Inventors: Jaroslav Tupy, Praha (CZ); Otto Louda, Pencin u Liberce (CZ); Jan Zima, Turnov (CZ)

(73) Assignee: Institute of Experimental Botany (UEB), Praha (CZ)

( * ) Notice: Subject to any disclaimer, the term of this patent is extended or adjusted under 35 U.S.C. 154(b) by 46 days.

(21) Appl. No.: 11/521,825

(22) Filed: Sep. 15, 2006

(65) Prior Publication Data

US 2008/0184403 P1 Jul. 31, 2008

(51) Int. Cl.
*A01H 5/00* (2006.01)

(52) U.S. Cl. ..... Plt./161

(58) Field of Classification Search ..... Plt./161
See application file for complete search history.

(56) References Cited

PUBLICATIONS

UpovROM search plant variety database for cultivar Orion UEB 2718/1.*

Usov A.G. Krymskaya opytnaya stantsiya sadovodstva Malen'koe Simferopol Ukrainian SSR Sadovodstvo (3) abstract.*

* cited by examiner

*Primary Examiner*—Annette H Para

(74) *Attorney, Agent, or Firm*—The Webb Law Firm

(57) ABSTRACT

A new and distinct *Malus Mill.* plant that produces large, juicy apples having an excellent sugar-acid balance and good keeping quality, suitable for use as a dessert fruit.

5 Drawing Sheets

Botanical classification: *Malus Mill.*
Varietal denomination: 'Orion'.

BACKGROUND OF THE INVENTION

The present invention comprises a new and distinct cultivar of apple tree botanically classified as *Malus Mill.* and known by the varietal name 'Orion'. The new variety was discovered in 1997 in The Czech Republic. The new variety is the result of a cross between 'Golden Delicious' (female parent, unpatented) and 'Otava' (male parent, unpatented). The purpose of the breeding program was to develop late disease resistant varieties of a high fruit quality that are also suitable for organic fruit production. The new variety exhibits similar ground color to its parents, but exhibits triploidy, a stronger tree vigor, and very low pollen fertility compared to both parents. Further, the new variety differs from 'Golden Delicious' in its broad globose fruit form versus the conical form of 'Golden Delicious' and the presence of $V_f$-resistance against scab exhibited by 'Orion'. 'Orion' also has a larger fruit size than 'Otava', but shares the traits of $V_f$-resistance against scab and the absence or weakness of skin greasiness to its male parent.

The new variety can also be compared to a *Malus Mill.* variety named 'Sirius' (U.S. Plant Pat. No. 18,541) as follows:

Similarities

Ramified tree type;

Triploid varieties with low pollen fertility;

Yellow ground color of fruits;

Overcolor absent or very low;

Absence of bloom and greasiness of fruit skin;

Fruit russeting around eye basin and on cheeks absent or very low;

Yellowish color of the flesh; and $V_f$-resistance against scab.

Differences

Tree vigor medium to strong versus strong with 'Sirius';

Flower size medium to large versus medium with 'Sirius';

Fruit shape broad globose versus globose to globose conical with 'Sirius';

Fruit ratio length/width small to medium versus medium with 'Sirius';

Length of stalk medium to long versus long with 'Sirius';

Depth of stalk cavity deep versus medium with 'Sirius';

Firmness of the flesh medium versus medium to firm with 'Sirius'; and

Time of maturing medium versus late with 'Sirius'.

The following characteristics also distinguish the new variety from other *Malus Mill.* varieties known to the breeders:

Late, dessert-type, triploid variety with good keeping quality;

Trees exhibit medium to strong vigor with an upright to spreading habit;

Low pollen fertility;

Large and broad globose fruits;

Bloom and greasiness of the skin is absent or very weak;

Ground color of fruit skin is yellow with an overcolor absent or very low and light red to orange red in color;

Low amount of russet on skin;

Fruits do not drop when ripe;

Flesh is yellowish in color, medium to firm, very juicy, highly well-balanced in sugar and acid content with a rich specific flavor; and $V_f$-resistance against scab.

The new variety has been trial and field tested and has been found to retain its distinctive characteristics and remain true to type through successive asexual propagations via budding and grafting on apple tree rootstocks.

DESCRIPTION OF THE DRAWINGS

The accompanying photographic drawings illustrate the new cultivar, with the color being as nearly true as is possible with color illustrations of this type. It should be noted that colors may vary with growing conditions and time of year.

DESCRIPTION OF THE PLANT

Figure 1:
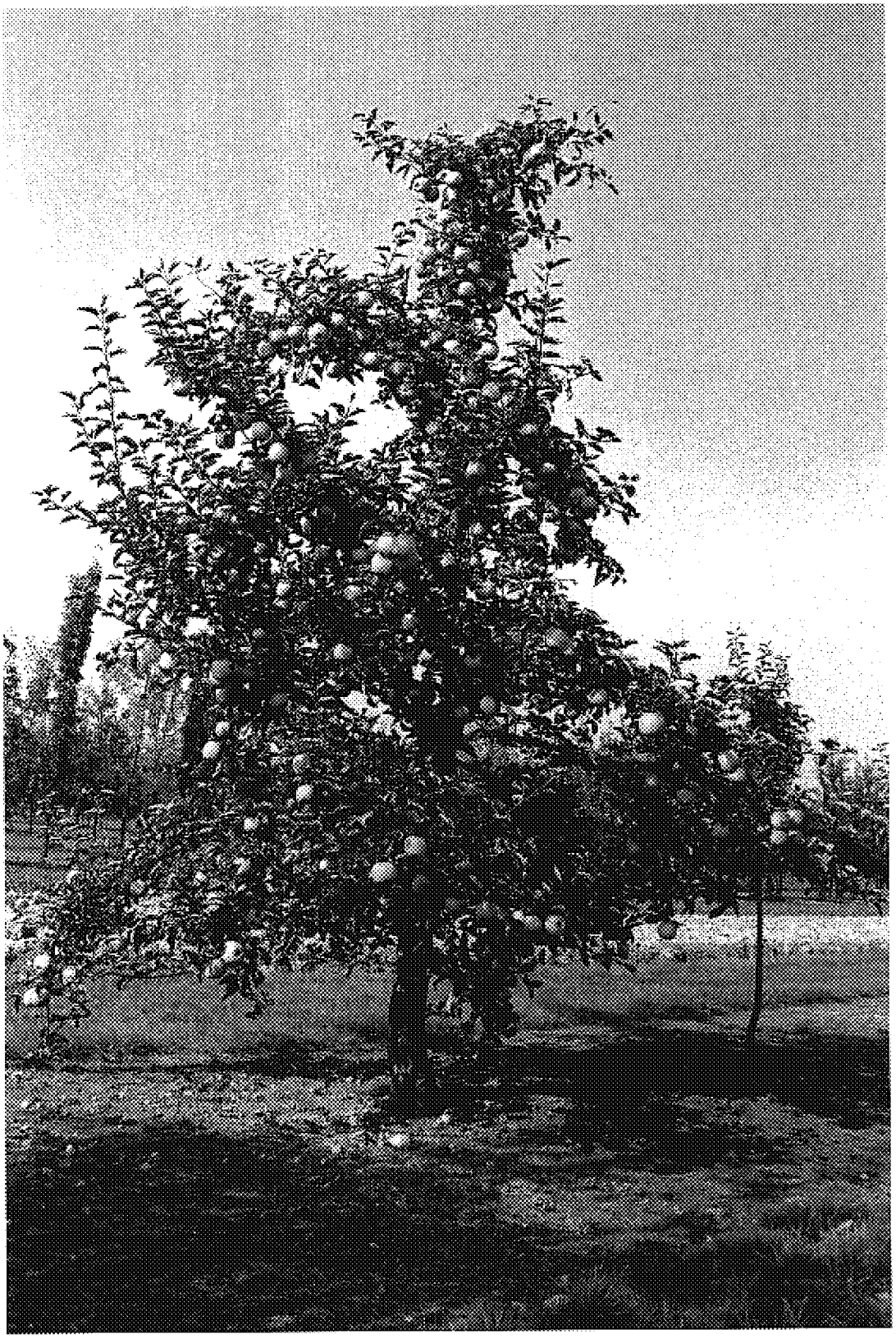
FIG. 1 is a photograph of the tree of the new variety on seedling rootstock, showing canopy form and uniformly sized fruits at maturity.
Figure 2:
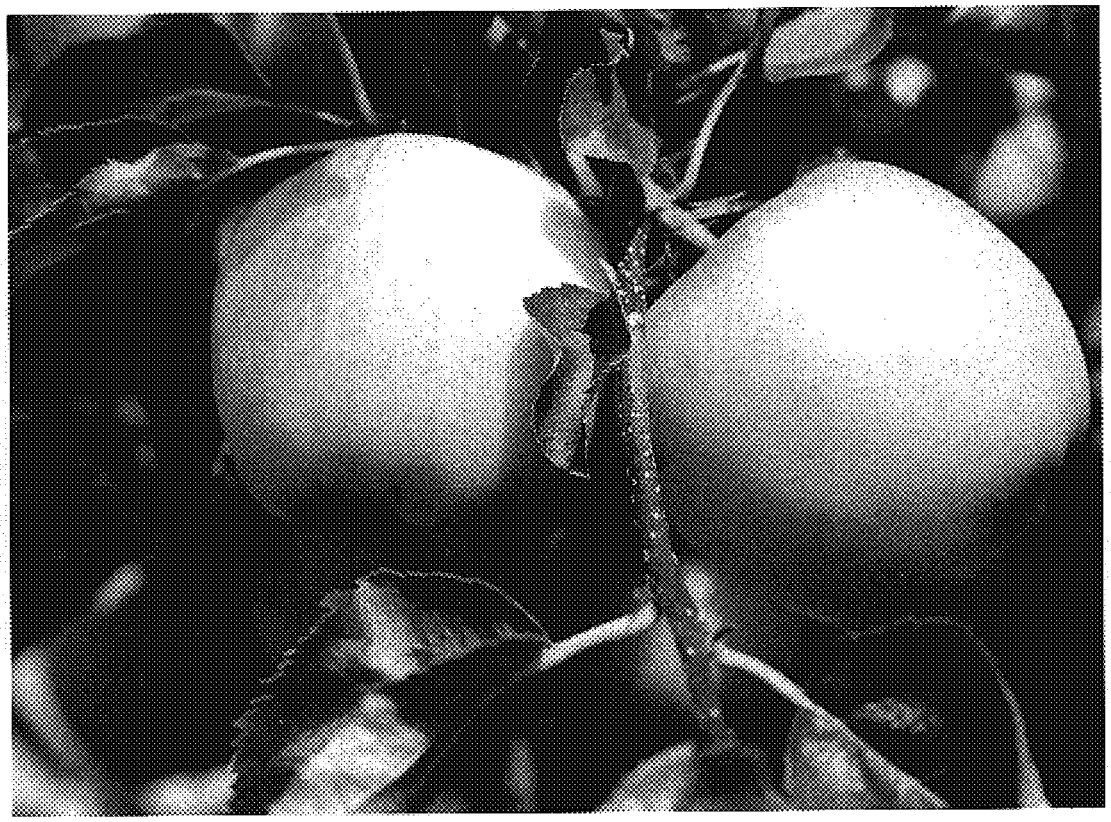
FIG. 2 shows a close-up view of the fruits of the new variety at maturity.
Figure 3:
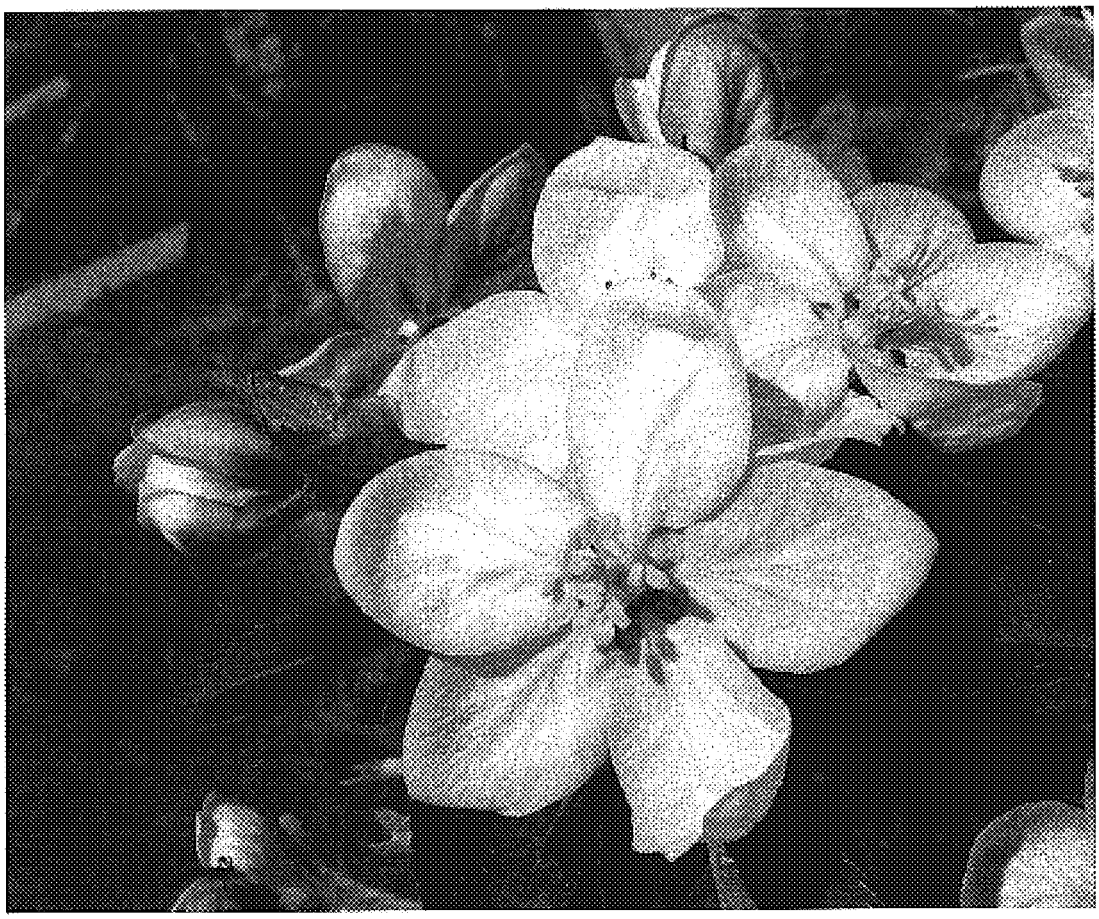
FIG. 3 shows the blossoms of the new variety.
Figure 4:
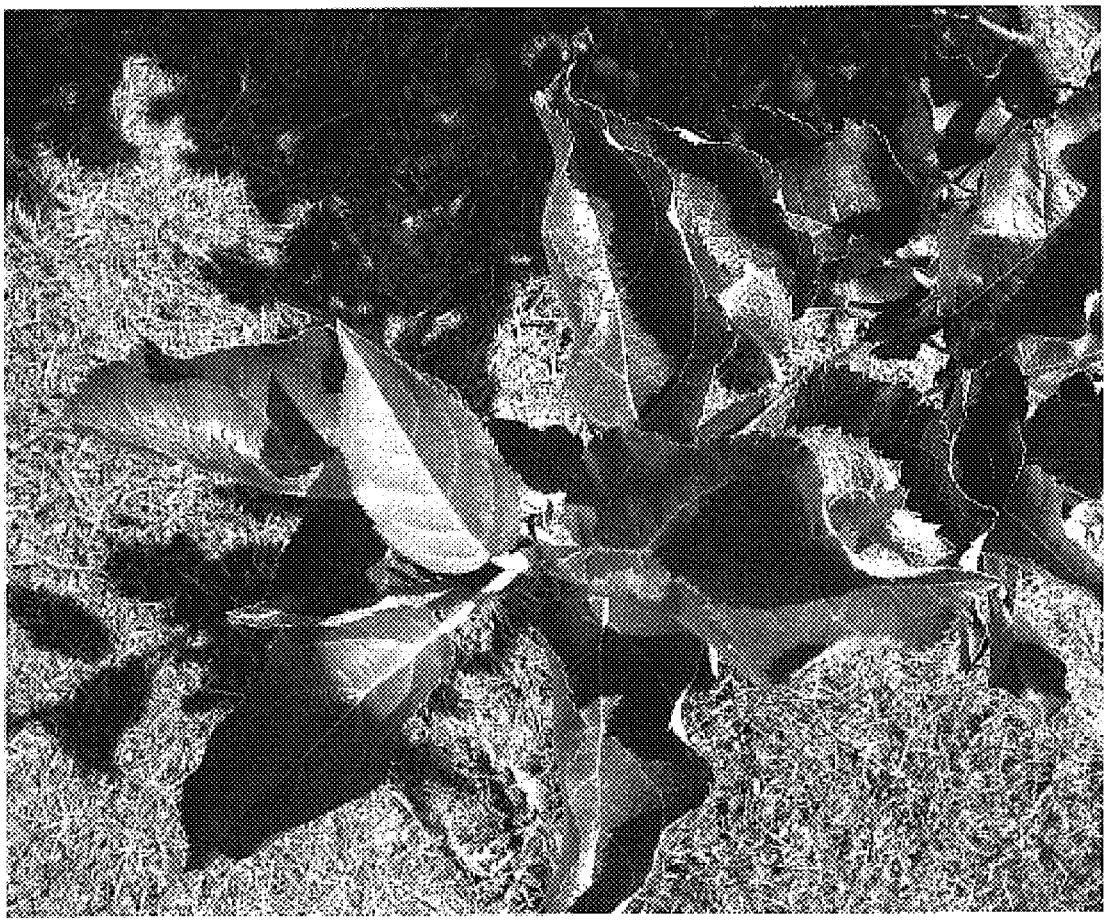
FIG. 4 shows the growing shoot of the new variety.
Figure 5:
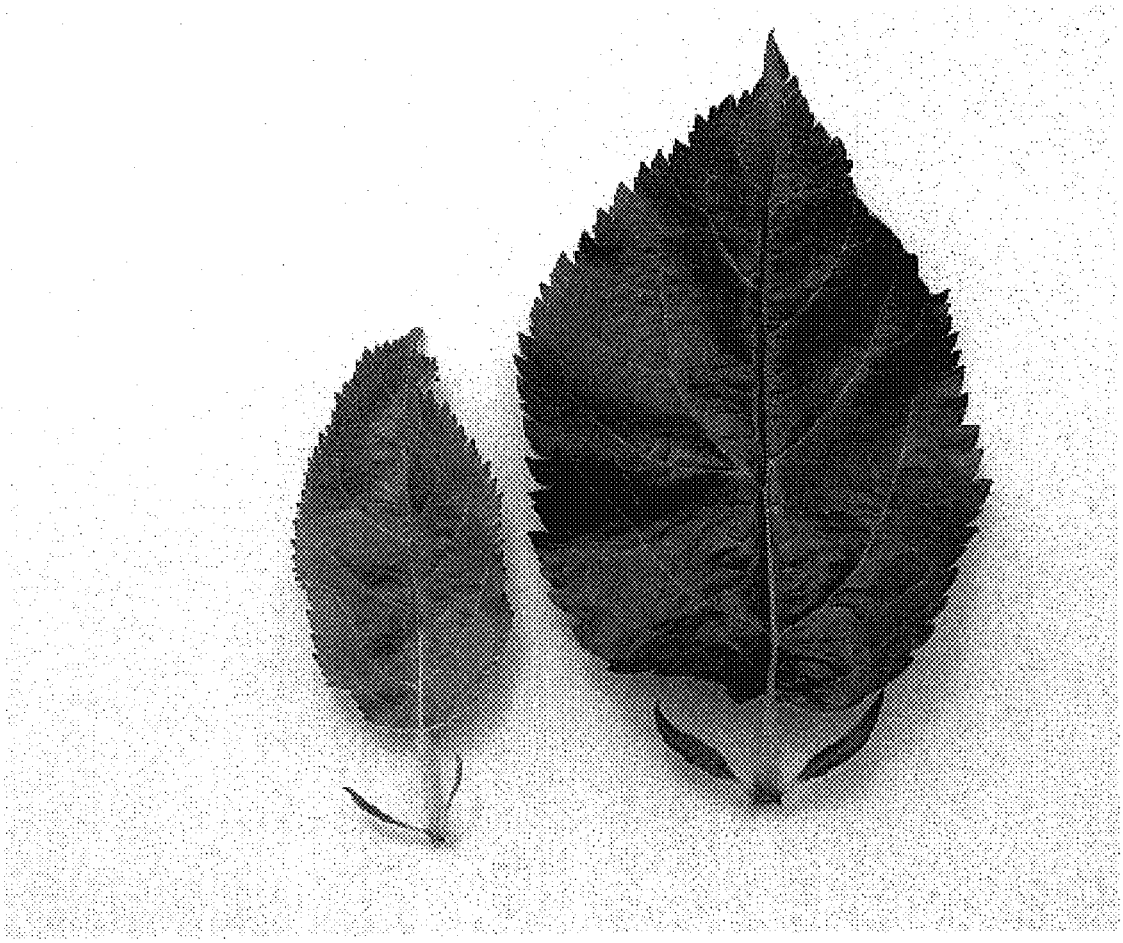
FIG. 5 shows a close-up view of the young and mature leaves of the new variety.

The following detailed description sets forth the characteristics of the new cultivar. The data which defines these characteristics was collected by asexual reproductions by budding and grafting on apple tree rootstocks first carried out in The Czech Republic in the Spring of 1998. The new variety was grafted on M9 rootstock and grown under natural field conditions without irrigation. The following fertilizer combination was used (Kg/ha/year): 55 parts nitrogen, 25 parts phosphorous, 60 parts potassium, 55 parts calcium, and 5 parts magnesium. Color references are primarily to the R.H.S. Colour Chart of The Royal Horticultural Society of London.

TREE

Age: 6 years after grafting on M9 rootstock.
Size: 3.0 m high, 2.3 m wide.
Vigor: Medium to strong.
Density: Open.
Form: Upright to spreading.
Production: High with annual bearing.
Growth type: Ramified.
Bearing: Annual.
Trunk:
- *Size.*—Approximately 7.5 cm in diameter at 30 cm from the soil line.
- *Surface texture.*—Slightly rough.
- *Bark color.*—197B.
- *Lenticels (150 cm above ground).*—Length: Up to 4 mm. Width: 0.8 mm. Color: 150A to 156B. Density: 3 lenticels per $cm^2$.

Branches:
- *Diameter.*—Main branches at the trunk are 3.0–4.0 cm.
- *Surface texture.*—Smooth, becoming slightly rough with age.
- *Color.*—One year: 200B/C. Two year: 197A/B.
- *Form.*—Moderately branching.
- *Average crotch angle.*—70 to 80 degrees.
- *Bud arrangement.*—Alternate. Internode: 3.0 cm.
- *Lenticels (on 1 year shoot).*—Length: 0.5–1.1 mm. Width: 0.5–0.9 mm. Shape: Round to oval. Density: Dense, 8 to 10 lenticels per $cm^2$. Color: 156C.

Leaves (measured at the middle of growing shoot):
- *Length.*—About 85 mm to about 115 mm, averaging about 95 mm.
- *Width.*—About 60 mm to about 80 mm, averaging about 65 mm.
- *Form.*—Ovate to lanceolate.
- *Texture.*—Smooth.
- *Thickness.*—Moderately thick.
- *Base.*—Mostly symmetric.
- *Apex.*—Acute.
- *Margin.*—Complex, sharply serrate.
- *Pubescence.*—Upper surface: None present. Lower surface: Very fine.
- *Color.*—Young leaves: Upper surface: 146B. Lower surface: 148C. Mature leaves: Upper surface: 147A. Lower surface: 148B.
- *Petiole.*—Shape: Straight to slightly bent, thickening towards the base. Length: About 20 mm to about 30 mm, averaging about 26 mm. Diameter: About 2.5 mm in the middle. Color: 144C with slight 58A at the base.
- *Veins.*—Venation type: Net-like, medium dense. Color: Upper surface: 144B. Lower surface: 145B/C.

Flower buds (popcorn stage):
- *Pedicel.*—Length: Typically in the range of 25–35 mm. Diameter: 1.8–1.9 mm. Color: 146B/C.
- *Bud.*—Length: About 13 mm. Width: 10–11 mm. Color: 64C/D.

Flowers:
- *Bloom timing.*—1 to 2 days before 'Golden Delicious'.
- *Blooming period.*—Medium to long.
- *Pollination requirements.*—Triploid, self-sterile, needs good pollinators.
- *Number of flowers per cluster.*—5.
- *Fragrance.*—Faint.
- *Petals.*—Number: 5. Length: 25–26 mm. Width: 18 mm. Shape: Broadly ovate. Aspect: Position predominantly overlapping. Margin: Entire. Texture and appearance: Soft and smooth. Color: When opening: Upper surface: 75B to 75D. Lower surface: 75A to 75D. Fully opened: Upper surface: 155C and 69D. Lower surface: 155C and 69B as venation and blush.
- *Sepals.*—Shape: Elongated conical. Margin: Entire. Texture: Finely pubescent. Length: 13–15 mm from the union. Width: Typically 4 mm at the middle. Color: Upper surface: 144A/B, tip 60A. Lower surface: 144A, tip 60A.
- *Stamens.*—Number (per flower): About 19. Filament length: 6–13 mm.
- *Anthers.*—Shape: Oval. Length: 3 mm. Color: 10A/B.
- *Pollen.*—Color: 11A. Amount (generally): Medium.
- *Pistils.*—Length: 17 mm.
- *Style.*—Length: 13–14 mm. Color: 144B/C.
- *Stigma.*—Shape: Rounded. Color: 153A.

Fruit:
- *Maturity when described.*—Eating maturity — after 2 months in common storage.
- *Date of picking.*—Oct. 17, 2005.
- *Size.*—Axial diameter: Average 74 mm. Transverse diameter: Average 83 mm.
- *Form.*—Broad globose, very weak ribbing, slight calyx lobes.
- *Cavity.*—Shape: Acuminate, russeted surface. Depth: Typically between 16–20 mm. Breadth: Typically between 32–36 mm.
- *Basin.*—Shape: Wide, medium deep, smooth, slightly ribbed. Depth: Typically between 9–11 mm. Width: Typically between 26–30 mm.
- *Calyx.*—Narrowly lanceolate, wide, open.

Skin:

*Thickness.*—Medium.

*Texture.*—Smooth, occasionally with fine russet, without greasiness.

*Tendency to crack.*—Absent.

*Color.*—Overcolor absent or occasionally as a low 35A to 48B blush.

*Ground color.*—13A/B.

Flesh:

*Aroma.*—Medium.

*Color.*—14D.

*Texture.*—Medium firm, fine grained, very juicy.

*Eating quality.*—Very good, complex distinctive flavor combining sweetness (16% Brix) and tartness.

Core:

*Bundle area.*—On longitudinal section defined with vascular strands onion shaped to oval, width 30 mm, length 28 mm, core locules open.

*Bundle.*—Vascular strands medium distinct.

*Calyx tube.*—Cylindrical, very short.

*Styles.*—Dry remnants present.

*Stamens.*—Dry remnants present.

*Seed cells.*—Wall: Slightly cracked. Depth: About 10 mm. Breadth: About 5 mm. Longitudinal section: About 19 mm (length of seed cell).

Seeds:

*Number perfect.*—2 to 5.

*Number in one cell.*—0 to 2.

*Length.*—About 9.5 mm.

*Breadth.*—About 4 mm.

*Form.*—Acute, can be flattened.

*Color.*—166A to 175A.

Stem:

*Length.*—Typically between 20 and 30 mm.

*Width.*—About 2 mm.

*Color.*—Green to brown.

Use: Late very good dessert variety suitable for both conventional and organic growing as well as for home gardens.

Shipping quality: Good.

Keeping quality: Good, at least 4 months in common storage.

Tree winter hardiness: No frost damage observed at the place of origin, lowest winter temperatures approximately −20° C.

Bud winter hardiness: No frost damage observed at the place of origin, lowest winter temperatures approximately −20° C.

Drought tolerance: Unknown.

Disease resistance: $V_f$-resistance against scab.

I claim:

1. A new and distinct variety of *Malus Mill.* plant substantially as is herein described and illustrated.

* * * * *